United States Patent [19]

Markley

[11] 3,954,440

[45] May 4, 1976

[54] SUBSTITUTED 2-HYDROXY-2-PHENYLBUTYLSULFONATE COMPOUNDS

[75] Inventor: Lowell D. Markley, Midland, Mich.

[73] Assignee: The Dow Chemical Company, Midland, Mich.

[22] Filed: Mar. 10, 1975

[21] Appl. No.: 556,605

Related U.S. Application Data

[62] Division of Ser. No. 466,568, May 3, 1974, Pat. No. 3,900,509.

[52] U.S. Cl. .............................. 71/103; 260/456 R; 260/456 P; 260/456 A; 260/488 CD; 260/618 D

[51] Int. Cl.$^2$ ........................................... A01N 9/14

[58] Field of Search ..................... 260/456 R, 456 P; 71/103

[56] References Cited
OTHER PUBLICATIONS

Mitsui et al., Chem. Abstracts, 63, 4133(f), (1965).

Primary Examiner—James O. Thomas, Jr.
Assistant Examiner—G. Breitenstein
Attorney, Agent, or Firm—Gary D. Street; Edward E. Schilling; James W. Ambrosius

[57] ABSTRACT

Disclosed herein are substituted 2-hydroxy-2-phenylbutylsulfonate compounds which are useful as herbicides.

21 Claims, No Drawings

SUBSTITUTED 2-HYDROXY-2-PHENYLBUTYLSULFONATE COMPOUNDS

This is a division of application Ser. No. 466,568 filed May 3, 1974 now U.S. Pat. No. 3,900,509.

SUMMARY OF THE INVENTION

The present invention is directed to novel substituted 2-hydroxy-2-phenylbutylsulfonate compounds of the following formula:

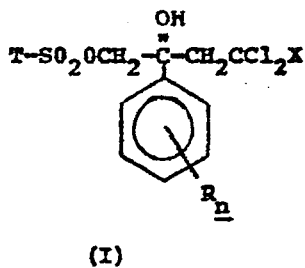

(I)

wherein X represents hydrogen, chloro or methyl; $n$ represents an integer of 0 to 3, inclusive; R is ring-substituted in the 3, 4 or 5 ring position and each R independently represents trifluoromethyl, alkyl of from 1 to about 3 carbon atoms, bromo, chloro, fluoro, nitro or alkoxy of from 1 to about 3 carbon atoms; T represents alkyl of from 1 to about 18 carbon atoms, haloalkyl of from 1 to about 4 carbon atoms, benzyl, substituted benzyl, phenyl, substituted phenyl or

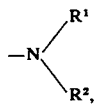

and $R^1$ and $R^2$ each independently represent hydrogen or alkyl of from 1 to about 3 carbon atoms.

The compounds of the above Formula I, hereinafter referred to for convenience as "active ingredients", have been found to be active as herbicides in the pre- and post-emergent control of undesired vegetation. Accordingly, the present invention also encompasses compositions containing one or more active ingredients as well as methods of controlling undesired plants. Such methods comprise applying a herbicidally-effective amount of one or more active ingredients to the locus of the undesired plants, that is, the seeds, foliage or other part of the growing plants or soil in which the plants are growing or would grow.

DETAILED DESCRIPTION

The term "alkyl" as used herein and in the appended claims is employed to designate a straight- or branched-chain radical containing, where not otherwise expressly defined, from 1 to about 18 carbon atoms, such as, for example, methyl, ethyl, propyl, isopropyl, butyl, tert.-butyl, pentyl, hexyl, heptyl, octyl, nonyl, decyl, tetradecyl, pentadecyl, hexadecyl, heptadecyl, octadecyl and the like including the various homologues and isomers of alkyl having from 1 to about 18 carbon atoms. The term "halo" as employed herein means bromo, chloro or iodo. The term "halo alkyl" is employed herein to designate groups such as, for example, chloromethyl, iodomethyl, bromomethyl, chloroethyl, bromoethyl, iodoethyl, trichloromethyl, dibromoethyl, tribromomethyl, di-iodoethyl, chloro-n-propyl, bromo-n-propyl, iodoisopropyl, bromo-tert-butyl, 1,3,3-trichlorobutyl, 1,3,3-tribromobutyl and the like. As used herein the term "alkoxy" can be methoxy, ethoxy, n-propoxy and isopropoxy. The "substituted phenyl" and "substituted benzyl" terms as employed herein refer to phenyl or benzyl radicals substituted by one or more, preferably from one to about three, nitro groups, halo groups or alkyl groups of from 1 to about 4 carbon atoms.

The term "herbicide" is used herein to mean an active ingredient which controls or modifies the growth of plants. By a "growth-controlling" or "herbicidally-effective" amount is meant an amount of active ingredient which causes a modifying effect and includes deviations from natural development, such as, for example, killing, retardation, defoliation, desiccation, regulation, stunting, tillering stimulation, dwarfing and the like. The term "plants" is meant to include germinant seeds, emerging seedlings and established vegetation, including the roots and above-ground portions thereof.

The active ingredients of the present invention are usually obtained as crystalline solids which are soluble in many organic solvents commonly employed as herbicidal carriers. The active ingredients of the present invention are suitable for use as herbicides, especially as pre-emergent herbicides. Certain of the active ingredients have been found to be particularly useful as selective herbicides in the presence of desired standing or seeded crops. The active ingredients of Formula I wherein $n$ is 0 constitute a preferred embodiment of the present invention. Another preferred class of active ingredients are those of Formula I wherein $n$ is 1. A further preferred embodiment includes active ingredients of Formula I wherein $n$ is 2. Active ingredients of Formula I wherein $n$ is 3 constitute still another preferred embodiment. In other preferred embodiments, T represents alkyl and $n$ represents the integer 0, 1, 2 or 3, respectively. Active ingredients of Formula I wherein X is chloro and $n$ is the integer 0, 1, 2 or 3, respectively, constitute further preferred embodiments of the invention.

In still another preferred embodiment, T is haloalkyl, further preferred are active ingredients wherein T is haloalkyl and $n$ is 0. Further preferred embodiments include active ingredients wherein T is selected from the group consisting of phenyl, substituted-phenyl, benzyl and substituted-benzyl and $n$ is 0, 1, 2 or 3, respectively. In such preceding embodiments, phenyl and substituted-phenyl are especially preferred. In additional preferred embodiments, T represents

and $n$ represents the integer 0, 1, 2 or 3, respectively. Especially preferred embodiments of the present invention include those respective active ingredients wherein X is chloro, $n$ is 1, R is halo and is substituted in the 3-ring position and wherein X is chloro, $n$ is 2, R is halo and such R groups are substituted in the 3, 5-ring positions. Other especially preferred embodiments include those respective active ingredients of Formula I wherein X is chloro, $n$ ;8c is 1, R is alkyl and is substituted in the 3-ring position and those wherein X is chloro, n is 2, R is alkyl and said R groups are substituted in the 3,5-ring positions. Particularly preferred embodiments include those respective active ingredients wherein T is alkyl, X is chloro, n is 1 or 2, R is bromo, chloro, fluoro or alkyl and is respectively substituted in the 3- or 3,5-ring positions.

The active ingredients of the present invention are prepared by reacting a selected substituted phenyl-2-hydroxybutanol reactant with a selected substituted sulfonyl halide reactant. The reaction, which is ordinarily carried out in the presence of an inert carrier medium, can be schematically illustrated as follows:

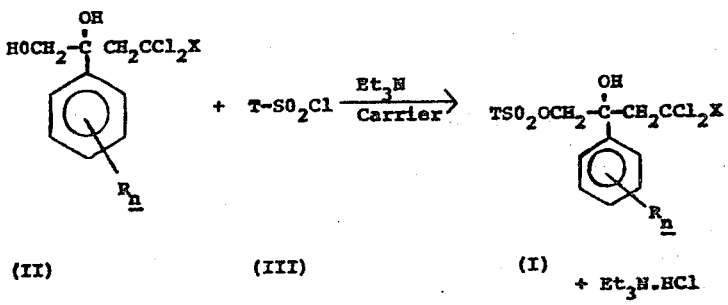

The X, R, n and T substituents in the above formulas are as previously defined. The hydrogen chloride liberated during the reaction is removed by use of binding agents such as triethylamine, calcium carbonate and the like. Generally, equimolar amounts of the reactants and binding agent are employed. Representative carrier media include, for example, those such as acetone, benzene, methylene chloride, chloroform or the like.

In carrying out the reaction, the substituted phenyl-1,2-butanediol reactant is mixed with the carrier medium and the binding agent added thereto. The resulting mixture is cooled in an ice-alcohol bath to a temperature below about 0° C., generally from about 0 to about −10° C., and a solution of the substituted sulfonyl halide reactant in a portion of the carrier medium is added dropwise thereto. The reaction mixture is agitated and the temperature is maintained below about 0° C. during the addition. Following the completion of the sulfonyl halide reactant addition, the reaction mixture is allowed to warm to ambient temperatures. The reaction mixture is subsequently washed with water, then with a 10% solution of sodium carbonate, and again with water. The organic product layer is separated and the same is dried over sodium sulfate, filtered, and the reaction mixture volume is reduced by removing most or all of the carrier medium present in vacuo. The resulting solid product residue is recovered and can be further purified by recrystallization from a solvent, such as tetrachloroethylene or one of those mentioned herein before. Where the product residue is an oil, the same can be treated with a benzenehexane mixture to crystallize the product.

The following examples illustrate the present invention and the manner by which it can be practiced but, as such, are not to be construed as limitations upon the overall scope of the same.

EXAMPLE 1

4,4,4-Trichloro-2-phenyl-2-hydroxybutanol (160 grams; 0.60 mole) was mixed with about 2000 milliliters (ml.) of methylene chloride and triethylamine (63.6 grams; 0.63 mole) was added thereto. The resulting mixture was cooled in an ice-methanol bath to a temperature of about −6 to about −8° C. Methanesulfonyl chloride (69 grams; 0.60 mole) in about 250 ml. of methylene chloride was added dropwise to the stirred reaction mixture over a period of about 45 minutes. The reaction mixture temperature was maintained below about 0° C. during the addition and, following the completion of the methanesulfonyl chloride solution; the reaction mixture temperature was allowed to come to room temperature. Thereafter, the reaction mixture was washed with water (four - 700 ml. portions), then with 700 ml. of a 10% sodium carbonate solution, and finally with another 700 ml. portion of water. An additional 600 ml. of methylene chloride was added to the organic product layer which was then dried over sodium sulfate. The volume of the organic product mixture was reduced to about 400 ml. by evaporation of the carrier medium in vacuo. The resulting white product precipitate was obtained by filtration. As a result of such operations, the desired 4,4,4-trichloro-2-phenyl-2-hydroxybutyl 1-methanesulfonate product was obtained as a white crystalline solid having a melting point of 128°–130° C.

EXAMPLE 2

4,4,4-Trichloro-2-(3,5-dichlorophenyl)-2-hydroxybutanol (5.2 grams, 0.015 mole) was dissolved in 75 ml. of methylene chloride and triethylamine (1.61 gram; 0.016 mole) added thereto. The resulting mixture was cooled in an ice-methanol bath to below about 0° C. and a solution of methane-sulfonyl chloride (1.83 gram; 0.016 mole) in 25 ml. of methylene chloride was added dropwise thereto. Following the completion of the methane-sulfonyl addition, the reaction mixture was stirred at ambient temperatures for a period of about 16 hours and then diluted with 100 ml. of methylene chloride and washed successively with water (2-100 ml. portions), 100 ml. of a 10% Na$_2$CO$_3$ solution and another 100 ml. of water. The organic product layer was dried over sodium sulfate and the carrier medium was removed in vacuo, leaving an oily residue. The oily residue was mixed with a benzene-hexane mixture to give the desired product as white solid, which was subsequently recrystallized twice from a benzene-hexane mixture. As a result of such operations, the desired 4,4,4-trichloro-2-(3,5-dichlorophenyl)-2-hydroxybutyl 1-methanesulfonate product was obtained as a white solid having a melting point of 99°–104° C.

Other active ingredients of the present invention are similarly prepared by employing procedures analogous to those set forth in the above examples and the foregoing teachings of the specification by reacting a selected substituted phenyl-2-hydroxybutanol reactant of Formula II with a selected substituted sulfonyl halide reactant of Formula I. Such other active ingredients include, inter alia, the following:

4,4,4-trichloro-2-phenyl-2-hydroxybutyl 1-benzenesulfonate, having a melting point of 103.5° – 105.5° C.;

4,4,4-trichloro-2-phenyl-2-hydroxybutyl 1-(4-methylbenzenesulfonate), having a melting point of 121° – 123° C.;

4,4,4-trichloro-2-hydroxy-2-phenylbutyl 1-(4-bromobenzenesulfonate), having a melting point of 127° – 128° C.;

4,4,4-trichloro-2-hydroxy-2-phenylbutyl 1-hexadecanesulfonate, having a melting point of 53.5° – 54.5° C.;

4,4,4-trichloro-2-hydroxy-2-phenylbutyl 1-(4-nitrobenzenesulfonate), having a melting point of 109.5° – 110.5° C.;

4,4,4-trichloro-2-hydroxy-2-phenylbutyl ethanesulfonate, having a melting point of 72° – 74° C.;

4,4,4-trichloro-2-hydroxy-2-phenylbutyl 1-benzenemethanesulfonate, having a melting point of 145° – 146.5° C.;

4,4,4-trichloro-2-hydroxy-2-phenylbutyl methylsulfonate, having a melting point of 101.5° – 102° C.;

4,4,4-trichloro-2-hydroxy-2-phenylbutyl 1-(3-chloropropanesulfonate), having a melting point of 78.5° – 80° C.;

4,4,4-trichloro-2-(3-chlorophenyl)-2-hydroxybutyl methanesulfonate, having a melting point of 111° – 113° C.;

4,4,4-trichloro-2-hydroxy-2-phenylbutyl 1-butanesulfonate, having a melting point of 54.5° – 57° C.;

4,4,4-trichloro-2-hydroxy-2-phenylbutyl 2-propane sulfonate, having a melting point of 74.5° – 76° C.;

4,4,4-trichloro-2-hydroxy-2-phenylbutyl sulfonate, having a melting point of 144° – 151° C.;

4,4,4-trichloro-2-hydroxy-2-phenylbutyl 1-(1-methylethylsulfonate), having a melting point of 85° – 95° C.;

4,4,4-trichloro-2-(3,5-dimethylphenyl)-2-hydroxybutyl methanesulfonate, having a melting point of 88° – 89.5° C.;

4,4-dichloro-2-(3,4,5-trimethylphenyl)-2-hydroxybutyl ethanesulfonate;

4,4,4-trichloro-2-hydroxy-2-(3,5-dichloro-4-methyl phenyl) 3-pentanesulfonate;

4,4-dichloro-2-(3,4,5-trichlorophenyl)-2-hydroxypentyl 1-propanesulfonate;

4,4,4-trichloro-2-(3,5-dimethoxyphenyl)-2-hydroxybutyl 1-nonanesulfonate;

4,4-dichloro-2-(3,5-bis(trifluoromethyl)phenyl)-2-hydroxybutyl 1-(3-bromopropanesulfonate);

4,4,4-trichloro-2-(3,5-dibromo-4-methylphenyl)-2-hydroxybutyl 1-octadecanesulfonate;

4,4-dichloro-2-(3,5-dinitrophenyl)-2-hydroxybutyl 1-hexanesulfonate;

4,4-dichloro-2-(3,5-diisopropylphenyl)-2-hydroxypentyl 1-(4-chlorobutanesulfonate);

4,4,4-trichloro-2-(3,5-dimethyl-4-(trifluoromethyl)-phenyl)-2-hydroxybutyl methanesulfonate;

4,4-dichloro-2-(4-nitrophenyl)-2-hydroxybutyl 1-(bromomethanesulfonate);

4,4-dichloro-2-(3-methyl-5-nitrophenyl)-2-hydroxypentyl 1-octanesulfonate;

4,4,4-trichloro-2-(5-chloro-3-methyl-4-nitrophenyl)-2-hydroxybutyl 1-methanesulfonate;

4,4-dichloro-2-(4-(trifluoromethyl)phenyl)-2-hydroxybutyl 1-(1,3,3-trichlorobutanesulfonate);

4,4-dichloro-2-(3-methoxyphenyl)-2-hydroxypentyl 1-dodecanesulfonate;

4,4,4-trichloromethyl-2-(3-fluoro-5-ethoxyphenyl)-2-hydroxybutyl 1-(1,3,3-trichloropropanesulfonate);

4,4-dichloro-2-(3,5-diisopropoxyphenyl)-2-hydroxybutyl 1-methanesulfonate;

4,4-dichloro-2-(3,4,5-trimethylphenyl)-2-hydroxypentyl 1-(3-chloropropanesulfonate);

4,4,4-trichloro-2-(3,4,5-tribromophenyl)-2-hydroxybutyl 1-(2,2-dibromoethanesulfonate);

4,4,4-trichloro-2-(3-fluoro-5-(trifluoromethyl)-phenyl)-2-hydroxybutyl 2-propanesulfonate;

4,4-dichloro-2-(3,4,5-trimethylphenyl)-2-hydroxybutyl 1-(pentachlorobenzenemethanesulfonate);

4,4,4-trichloro-2-(3,5-difluoro-4-methylphenyl)-2-hydroxybutyl 1-(3,4,5-trinitrobenzenemethanesulfonate);

4,4-dichloro-2-(3,4,5-trichlorophenyl)-2-hydroxypentyl 1-(pentachlorobenzenesulfonate);

4,4,4-trichloro-2-(3,5-dimethoxyphenyl)-2-hydroxybutyl 1-(3,4,5-tribromobenzenesulfonate);

4,4-dichloro-2-(3,5-bis(trifluoromethyl)phenyl)-2-hydroxybutyl 1-(3,4,5-tribromobenzenemethanesulfonate), 4,4,4-trichloro-2-(3,5-dibromo-4-methylphenyl)-2-hydroxybutyl 1-(2,4-dimethylbenzenemethanesulfonate);

4,4-dichloro-2-(3,5-dinitrophenyl)-2-hydroxybutyl 1-(2,4,6-trimethylbenzenesulfonate);

4,4-dichloro-2-(3,5-diisopropylphenyl)-2-hydroxypentyl 1-(3,5-dinitrobenzenesulfonate);

4,4,4-trichloro-2-(3,5-dimethyl-4-(trifluoromethyl)-phenyl)-2-hydroxybutyl 1-(2,4-dichloro-3,5-dimethylbenzenemethanesulfonate);

4,4-dichloro-2-(4-nitrophenyl)-2-hydroxybutyl 1-(3,5-dichloro-4-nitrobenzenemethanesulfonate);

4,4-dichloro-2-(3-fluoro-5-nitrophenyl)-2-hydroxypentyl 1-(2,4-dimethyl-6-nitrobenzenesulfonate);

4,4,4-trichloro-2-(5-chloro-3-methyl-4-nitrophenyl)-2-hydroxybutyl 1-(3,5-di-tert-butylbenzenemethanesulfonate);

4,4-dichloro-2-(4-fluoro-3-methoxyphenyl)-2-hydroxypentyl 1-(3,5-diiodo-2-methylbenzenemethanesulfonate);

4,4-dichloro-2-(4-(trifluoromethyl)-phenyl)-2-hydroxybutyl 1-(4-tert-butylbenzenesulfonate);

4,4,4-trichloro-2-(3-chloro-5-ethoxyphenyl)-2-hydroxybutyl 1-(2,6-dichloro-4-butylbenzenemethanesulfonate);

4,4-dichloro-2-(3,5-diisopropoxyphenyl)-2-hydroxybutyl 1-(2,4,6-trichlorobenzenemethanesulfonate);

4,4-dichloro-2-(3,4,5-trimethylphenyl)-2-hydroxypentyl 1-(3,5-diethylbenzenesulfonate);

4,4,4-trichloro-2-(3,4,5-tribromophenyl)-2-hydroxybutyl 1-(3,4,5-trichlorobezenesulfonate);

4,4-dichloro-2-hydroxy-2-(3,4,5-trimethylphenyl)-butylsulfamate;

4,4,4-trichloro-2-(3,5-dichloro-4-methylphenyl)-2-hydroxybutyl dimethylsulfamate;

4,4-dichloro-2-(3,4,5-trichlorophenyl)-2-hydroxypentyl ethylsulfamate;

4,4-dichloro-2-(3,5-bis(trifluoromethyl)-phenyl-2-hydroxybutyl diisopropylsulfamate;

4,4,4-trichloro-2-(3,5-dibromo-4-methylphenyl)-2-hydroxybutyl sulfamate;

4,4-dichloro-2-(3,5-dinitrophenyl)-2-hydroxybutyl sulfamate;

4,4-dichloro-2-(3,5-diisopropylphenyl)-2-hydroxypentyl methylsulfamate;

4,4,4-trichloro-2-(3,5-dimethyl-4-(trifluoromethyl)-phenyl)-2-hydroxybutyl ethylsulfamate;

4,4-dichloro-2-(3-methyl-5-nitrophenyl)-2-hydroxypentyl diethylsulfamate;

4,4,4-trichloro-2-(5-chloro-3-methyl-4-nitrophenyl)-2-hydroxybutyl dimethylsulfamate;

4,4-dichloro-2-(4-trifluoromethyl phenyl)-2-hydroxybutyl methylsulfamate;

4,4-dichloro-2-(3-methoxyphenyl)-2-hydroxypentyl sulfamate;

4,4,4-trichloro-2-(3-chloro-5-methoxyphenyl)-2-hydroxybutyl methylsulfamate;

4,4-dichloro-2-(3,5-dipropoxyphenyl)-2-hydroxybutyl n-propylsulfamate; and 4,4,4-trichloro-2-(3-bromo-5-(trifluoromethyl)-phenyl)-2-hydroxybutyl sulfamate.

The compounds of the present invention have been found to be suitable for use in methods for the pre- and post-emergent control of weeds or other unwanted vegetation. Certain of the active ingredients of the present invention have been found to be active against undesired vegetation in the presence of desired crop plants while giving little or no herbicidal action on the crop plants. For all such uses, unmodified active ingredients of the present invention can be employed. However, the present invention embraces the use of a herbicidally-effective amount of the active ingredients in composition form with an inert material known in the art as an adjuvant or carrier in solid or liquid form. Thus, for example, an active ingredient can be dispersed on a finely divided solid and employed therein as a dust. Also, the active ingredients, as liquid concentrates or solid compositions comprising one or more of the active ingredients, can be dispersed in water, typically with the aid of a wetting agent, and the resulting aqueous dispersion employed as a spray. In other procedures, the active ingredient can be employed as a constituent of organic liquid compositions, oil-in-water and water-in-oil emulsions, or water dispersions, with or without the addition of wetting, dispersing, or emulsifying agents.

Suitable adjuvants of the foregoing type are well known to those skilled in the art. The methods of applying the solid or liquid herbicidal formulations similarly are well known to the skilled artisan.

As organic solvents used as extending agents there can be employed hydrocarbons, e.g. benzene, toluene, xylene, kerosene, diesel fuel, fuel oil, and petroleum naphtha, ketones such as acetone, methyl ethyl ketone and cyclohexanone, chlorinated hydrocarbons such as carbon tetrachloride, chloroform, trichloroethylene, and perchloroethylene, esters such as ethyl acetate, amyl acetate and butyl acetate, ethers, e.g., ethylene glycol monomethyl ether and diethylene glycol monomethyl ether, alcohols, e.g., methanol, ethanol, isopropanol, amyl alcohol, ethylene glycol, propylene glycol, butyl Carbitol acetate and glycerine. Mixtures of water and organic solvents, either as solutions or emulsions, can be employed.

The active ingredients can also be applied as aerosols, e.g., by dispersing them by means of a compressed gas such as dichlorodifluoromethane or trichlorofluoromethane and other Freons and Genetrons, for example.

The active ingredients of the present invention can also be applied with solid adjuvants or carriers such as talc, pyrophyllite, synthetic fine silica, attapulgus clay, kieselguhr, chalk, diatomaceous earth, lime, calcium carbonate, bentonite, fuller's earth, cottonseed hulls, wheat flour, soybean flour, pumice, tripoli, wood flour, walnut shell flour, redwood flour and lignin.

As stated, it is frequently desirable to incorporate a surface active agent in the compositions of the present invention. Such surface active or wetting agents are advantageously employed in both the solid and liquid compositions. The surface active agent can be anionic, cationic or nonionic in character.

Typical classes of surface active agents include alkyl sulfonate salts, alkylaryl sulfonate salts, alkylaryl polyether alcohols, fatty acid esters of polyhydric alcohols and the alkylene oxide addition products of such esters, and addition products of long chain mercaptans and alkylene oxides. Typical examples of such surface active agents include the sodium alkylbenzene sulfonates having 10 to 18 carbon atoms in the alkyl group, alkylphenol ethylene oxide condensation products, e.g., p-isooctylphenol condensed with 10 ethylene oxide units, soaps, e.g., sodium stearate and potassium oleate, sodium salt of propylnaphthalene sulfonic acid, di(2-ethylhexyl)-ester of sodium sulfosuccinic acid, sodium lauryl sulfate, sodium decane sulfonate, sodium salt of the sulfonated monoglyceride of coconut fatty acids, sorbitan sesquioleate, lauryl trimethyl ammonium chloride, octadecyl trimethyl ammonium chloride, polyethylene glycol lauryl ether, polyethylene glycol esters of fatty acids and rosin acids, e.g., Ethofat 7 and 13, sodium N-methyl-N-oleyl taurate, Turkey Red Oil, sodium dibutyl naphthalene sulfonate, sodium lignin sulfonate, polyethylene glycol stearate, sodium dodecylbenzene sulfonate, tertiary dodecyl polyethylene glycol thioether (nonionic 218), long chain ethylene oxide-propylene oxide condensation products, e.g., Pluronic 61 (molecular weight 1000), polyethylene glycol ester of tall oil acids, sodium octyl phenoxyethoxyethyl sulfate, tris(polyoxyethylene)sorbitan monostearate (Tween 60), and sodium dihexyl sulfosuccinate.

The concentration of the active ingredients in solid or liquid compositions generally is from about 0.003 to about 95 percent by weight or more. Concentrations of from about 0.003 to about 50 weight percent are often employed. In compositions to be employed as concentrates, the active ingredient can be present in a concentration of from about 5 to about 98 weight percent. The active ingredient compositions can also contain other compatible additaments, for example, phytotoxicants, plant growth regulants, pesticides and the like and can be formulated with solid particulate fertilizer carriers such as ammonium nitrate, urea and the like.

The present compositions can be applied by the use of power-dusters, boom and hand sprayers, spray-dusters, by addition to irrigation water, and by other conventional means. The compositions can also be applied from airplanes as a dust or a spray since certain of the active ingredients are effective at low application rates.

The exact rate to be applied is dependent not only upon the specific active ingredient being employed, but also upon the particular plant species to be modified and the stage of growth thereof as well as the part of the plant to be contacted with the toxic active ingredient. Thus, it is to be understood that all of the active ingredients of the invention and compositions containing the same may not be equally effective at similar concentrations or against the same plant species. In non-selective pre-emergence and foliage treatments, the active ingredients of this invention are usually applied at an approximate rate of from about 1 to about 25 lbs. per acre, but lower or higher rates may be appropriate in some cases. In selective pre-emergence operations to foliage, a dosage of from about 0.13 to about 4.0 pounds per acre is usuallly employed but higher dosages may be necessary in some instances. In view of the foregoing and following disclosures, one skilled in the art can readily determine the optimum rate to be applied in any particular case.

So as to illustrate the general and selective herbidical properties of the active ingredients of the present invention, a group of controlled greenhouse experiments is described below.

EXAMPLE 3

Various species of plants were planted in beds of good agricultural soil in a greenhouse. After the plants had emerged and grown to a height of about 2–6 inches, certain of the plants were sprayed with a given volume of a solution containing 4000 parts per million of the candidate active ingredient, prepared by mixing the selected active ingredient and emulsifier or dispersant with water. Sufficient volumes of the solutions were applied to provide approximately 10.0 pounds of active ingredient per acre. Other plants were left untreated to serve as controls.

After a period approximately 14 days, the effect of each of the test ingredients on the plants was evaluated by a comparison with the control group of plants.

In such operations, each of the 4,4,4-trichloro-2-phenyl-2-hydroxybutyl 1-methanesulfonate (Compound A), 4,4,4-trichloro-2-phenyl-2-hydroxybutyl 1-benzenesulfonate (Compound B), 4,4,4-trichloro-2-phenyl-2-hydroxybutyl 1-(4-methylbenzenesulfonate) (Compound C), 4,4,4-trichloro-2-hydroxy-2-phenylbutyl 1-hexadecanesulfonate (Compound D) and 4,4,4-trichloro-2-phenyl-2-hydroxybutyl 1-(4-nitrobenzenesulfonate) (Compound E) test ingredients was found to give from 70 to 100 percent control of the growth of crabgrass, Johnson grass, barnyard grass and wild oats. In the same operations, each of the 4,4,4-trichloro-2-phenyl-2-hydroxybutyl 1-(methylsulfamate) (Compound F), 4,4,4-trichloro-2-phenyl-2-hydroxybutyl 1-(3-chloropropanesulfonate) (Compouond G), 4,4,4-trichloro-2-(3-chlorophenyl)-2-hydroxybutyl 1-methanesulfonate (Compound H) and 4,4,4-trichloro-2-(3,5-dichlorophenyl)-2-hydroxybutyl 1-methanesulfonate (Compound I) active ingredients was found to give from 70 to 100 percent control of the growth of crabgrass, barnyard grass, wild oats and yellow foxtail while each of the 4,4,4-trichloro-2-hydroxy- 2-phenylbutyl 1-butanesulfonate (Compound J), 4,4,4-trichloro-2-hydroxy-2-phenylbutyl 2-propanesulfonate (Compound K), and 4,4,4-trichloro-2-hydroxy-2-phenylbutyl 1-(1-methylethylsulfonate) (Compound L) active ingredients was found to give from 70 to 100 percent control of the growth of crabgrass and yellow foxtail. Further, in such operations, each of Compounds A, C, E, F, G and H were found to be substantially non-phytotoxic to cotton plants.

EXAMPLE 4

In representative pre-emergence operations, seeds of selected weed species are planted in seedbeds and, while exposed, sprayed with compositions containing an active test ingredient. The seeds are then covered with a layer of soil and the test beds maintained under conditions conducive to growth for a period of about 14 days. The test compositions are prepared as set forth hereinbefore. In such representative operations, each of Compounds A, B, C, D, E, G and J as set forth in Example 3 above and each of the active ingredients 4,4,4-trichloro-2-hydroxy-2-phenylbutyl 1-(4-bromobenzenesulfonate) (Compound M), 4,4,4-trichloro-2-hydroxy-2-phenylbutyl 1-benzenemethanesulfonate (Compound N), 4,4,4-trichloro-2-hydroxy-2-phenylbutyl sulfamate (Compound O) and 4,4,4-trichloro-2-hydroxy-2-phenylbutyl ethanesulfonate was found to give from 70 to 100% control of germination and growth of crabgrass, Johnson grass and barnyard grass seeds at an application rate of one pound per acre. None of the foregoing compounds was found to produce any significant phytotoxic effects on the germination and growth of cotton seeds. Compounds F, H, I and K from Example 3 above similarly were found to give from 70 to 100 percent control of the growth of crabgrass, barnyard grass, wild oat and yellow foxtail seeds at an application rate of ten pounds per acre; Compounds F and I exhibited no significant phytotoxic effects on the growth of cotton seeds at such application rate.

Certain of the above and other active ingredients of the present invention are also active against some or all of the above plant species and other plant species, such as, for example, pigweed, quackgrass, nutsedge, giant foxtail, bindweed and the like at various application rates. Certain of the active ingredients of the present invention also exhibit selective phytotoxic action against undesired vegetation in the presence of seeded or standing crops such as, for example, soybeans and corn.

The substituted sulfonyl halide reactants of Formula III which are employed as starting materials in the preparation of the active ingredients of the present invention are known and are either commercially available or can be readily prepared by those skilled in the art according to methods set forth or analogous to those set forth in the open literature. The substituted 2-phenyl-2-hydroxybutanol reactants of Formula II can be readily obtained according to the following general reaction sequence:

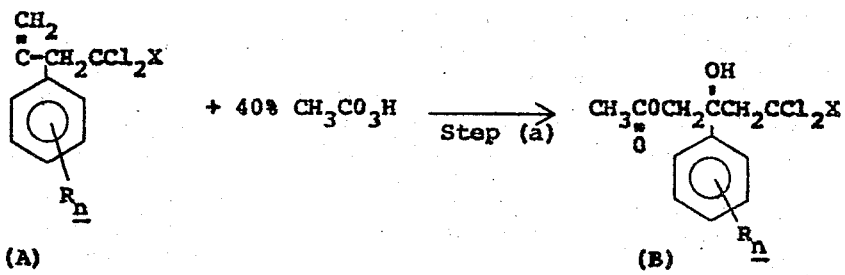

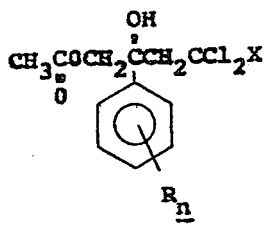

(B)

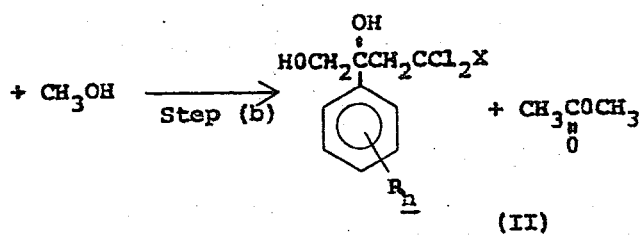

wherein X, R and *n* are as previously defined.

Step (a) of the reaction is usually carried out by mixing Reactant A with glacial acetic acid and adding concentrated sulfuric acid and the peracetic acid thereto. The resulting reaction mixture is usually heated at temperatures of from about 25° to about 65° C. for a period of from about 50 to about 100 hours. Generally, an excess amount of the peracetic acid is employed. The course of the reaction is monitored by determining the presence of peroxide present in the reaction mixture. Following the reaction period, the reaction mixture is diluted with water and a solvent, such as, for example, methylene chloride, and the organic layer is separated, washed with water and neutralized with a base, e.g., sodium carbonate and the like and dried over sodium sulfate. The solvent present in the mixture is removed in vacuo and the resulting residue, representing reactant (B), is mixed with methanol and a small amount of p-toluenesulfonic acid. The resulting mixture is refluxed for a period of from about 4 to about 24 hours, cooled, and mixed with water and methylene chloride. The organic layer is separated from the resulting mixture, washed with water and dried over sodium sulfate. The solvent is removed in vacuo to obtain a product residue representing reactant (II).

In view of the foregoing and the following specific repesentative example, the necessary starting materials of Formula II can be readily prepared by those skilled in the art.

EXAMPLE 5

α-(2,2,2-trichloroethyl)-3,5-dichlorostyrene (10.0 grams, 0.033 mole) was mixed with 75 ml. of glacial acetic acid and 10 drops of concentrated sulfuric acid and 16.5 ml. of 40% peracetic acid were added thereto. The resulting reaction mixture was heated at about 60° C., with stirring, for a period of about 72 hours. The reaction mixture was subsequently diluted with 200 ml. of water and 200 ml. of methylene chloride. The organic layer of the resulting mixture was separated and washed successively with 2–100 ml. portions of water, 2–100 ml. portions of a 10% sodium carbonate solution, 100 ml. portion of a 5% sodium bisulfite solution and another 100 ml. portion of water. The organic layer of the resulting mixture was separated therefrom, dried over sodium sulfate and the solvent removed in vacuo. The residual oil thus obtained was dissolved in about 75 ml. of methanol and 0.3 gram of p-toluenesulfonic acid were added thereto. The resulting mixture was heated under reflux conditions for a period of about 11 hours and then cooled and diluted with 200 ml. of water and 200 ml. of methylene chloride. The organic layer of the resulting mixture was separated, dried over sodium sulfate. The solvent was removed in vacuo to obtain the desired 4,4,4-trichloro-2-(3,5-dichlorophenyl)-2-hydroxybutanol product as a clear oily liquid.

What is claimed is:

1. A composition comprising a herbicidally-effective amount of a compound of the formula:

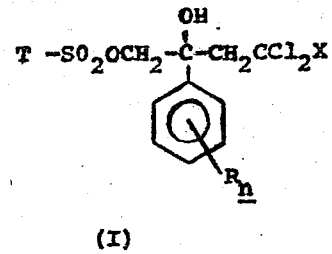

(I)

wherein X represents chloro, *n* represents an integer of 0 to 3, inclusive; R is ring-substituted in the 3, 4 or 5-ring position and each R independently represents trifluoromethyl, alkyl of from 1 to about 3 carbon atoms, bromo, chloro, fluoro, nitro or alkoxy of from 1 to about 3 carbon atoms; T represents alkyl of from 1 to about 18 carbon atoms, haloalkyl of from 1 to about 4 carbon atoms and an inert solid or liquid carrier therefor.

2. A composition according to claim 1 wherein a surface active agent is included.

3. The composition according to claim 1 wherein the compound is 4,4,4-trichloro-2-phenyl-2-hydroxybutyl 1-methanesulfonate.

4. The composition according to claim 1 wherein the compound is 4,4,4-trichloro-2-phenyl-2-hydroxybutyl 1-hexadecanesulfonate.

5. The composition according to claim 1 wherein the compound is 4,4,4-trichloro-2-phenyl-2-hydroxybutyl 1-butanesulfonate.

6. The composition according to claim 1 wherein the compound is 4,4,4-trichloro-2-phenyl-2-hydroxybutyl 2-propanesulfonate.

7. The composition according to claim 1 wherein the compound is 4,4,4-trichloro-2-phenyl-2-hydroxybutyl 1-(3-chloropropanesulfonate).

8. The composition according to claim 1 wherein the compound is 4,4,4-trichloro-2-(3-chlorophenyl)-2-hydroxybutyl 1-methanesulfonate.

9. The composition according to claim 1 wherein the compound is 4,4,4-trichloro-2-(3,5-dichlorophenyl)-2-hydroxybutyl 1-methanesulfonate.

10. The composition according to claim 1 wherein the compound is 4,4,4-trichloro-2-(3,5-dimethylphenyl)-2-hydroxybutyl 1-methanesulfonate.

11. The composition according to claim 1 together with a solid carrier.

12. The composition according to claim 1 together with a liquid carrier.

13. The method of controlling undesired plant growth which comprises applying to the locus of said plants a herbicidally-effective amount of a compound of the formula:

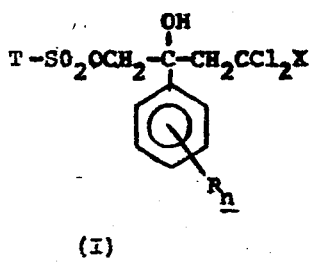

(I)

wherein: X represents chloro, n represents an integer of 0 to 3, inclusive; R is ring-substituted in the 3, 4 or 5-ring position and each R independently represents trifluoromethyl, alkyl of from 1 to about 3 carbon atoms, bromo, chloro, fluoro, nitro or alkoxy of from 1 to about 3 carbon atoms; T represents alkyl of from 1 to about 18 carbon atoms, haloalkyl of from 1 to about 4 carbon atoms.

14. The method according to claim 13 in which said compound is 4,4,4-trichloro-2-phenyl-2-hydroxybutyl 1-methanesulfonate.

15. The method according to claim 13 in which said compound is 4,4,4-trichloro-2-phenyl-2-hydroxybutyl 1-hexadecanesulfonate.

16. The method according to claim 13 in which said compound is 4,4,4-trichloro-2-phenyl-2-hydroxybutyl 1-butanesulfonate.

17. The method according to claim 13 in which said compound is 4,4,4-trichloro-2-phenyl-2-hydroxybutyl 2-propanesulfonate.

18. The method according to claim 13 in which said compound is 4,4,4-trichloro-2-phenyl-2-hydroxybutyl 1-(3-chloropropanesulfonate).

19. The method according to claim 13 in which said compound is 4,4,4-trichloro-2-(3-chlorophenyl)-2-hydroxybutyl 1-methanesulfonate.

20. The method according to claim 13 in which said compound is 4,4,4-trichloro-2-(3,5-dichlorophenyl)-2-hydroxybutyl 1-methanesulfonate.

21. The method according to claim 13 in which said compound is 4,4,4-trichloro-2-(3,5-dimethylphenyl)-2-hydroxybutyl 1-methanesulfonate.

* * * * *